US006248361B1

(12) United States Patent
Johnson et al.

(10) Patent No.: US 6,248,361 B1
(45) Date of Patent: Jun. 19, 2001

(54) WATER-SOLUBLE FOLIC ACID COMPOSITIONS

(75) Inventors: Bruce Johnson, Marion County; Vladimir Kuna, Washington County, both of OR (US)

(73) Assignee: Integ, Ltd., Tigard, OR (US)

( * ) Notice: Subject to any disclaimer, the term of this patent is extended or adjusted under 35 U.S.C. 154(b) by 0 days.

(21) Appl. No.: 09/505,057

(22) Filed: Feb. 16, 2000

Related U.S. Application Data

(60) Provisional application No. 60/122,168, filed on Feb. 26, 1999.

(51) Int. Cl.$^7$ .............................. A61K 9/20; A61K 9/14; A61K 9/50
(52) U.S. Cl. .................. 424/489; 424/464; 424/465; 424/499; 424/502
(58) Field of Search .................................. 424/464, 465, 424/489, 499, 502

(56) References Cited

U.S. PATENT DOCUMENTS

| 5,972,985 | * | 10/1999 | Thomas et al. | 514/400 |
| 6,046,177 | * | 4/2000 | Stella et al. | 514/58 |
| 6,071,539 | * | 6/2000 | Robinson et al. | 424/466 |

* cited by examiner

*Primary Examiner*—Thurman K. Page
*Assistant Examiner*—S. Tran
(74) *Attorney, Agent, or Firm*—Chernoff, Vilhauer, McClung & Stenzel, LLP

(57) ABSTRACT

Water-soluble folic acid compositions and pharmaceutical dosage forms comprising the compositions and methods for making the same are disclosed.

12 Claims, No Drawings

WATER-SOLUBLE FOLIC ACID COMPOSITIONS

The priority of Provisional Application Ser. No. 60/122,168 filed Feb. 26, 1999 is claimed.

BACKGROUND OF THE INVENTION

The invention concerns water-soluble compositions comprising folic acid and/or folic acid analogs, and at least one carbonate or bicarbonate material, methods for making such compositions, and methods for making pharmaceutical dosage forms thereof.

Folic acid has the empirical formula $C_{19}H_{19}N_7O_6$ and the structural formula shown below. It is a B vitamin that is found in liver, kidney, mushrooms, spinach, yeast, green leaves, and grasses. Pure folic acid crystals are yellowish-orange and only very slightly soluble in cold water (0.0016 mg/ml at 25° C.).

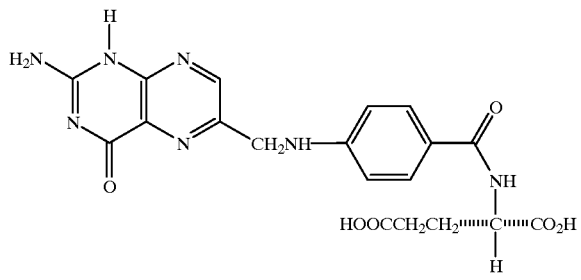

Absorption of folic acid by the body is facilitated by enzymes associated with the mucosal cell membrane. More specifically, absorption primarily occurs in the mucosae of the upper intestine, known as the jejunum and duodenum. Insufficient folic acid in the diet and the inability to absorb folic acid can cause anemia and/or birth defects, namely, anecephaly and spina bifida, the latter resulting in brain development abnormalities and even death.

Anecephaly and spina bifida are caused by neural tube defects and the frequency of these defects can be greatly decreased by supplementing the diets of pregnant women with folic acid. The discovery of the importance of folic acid stemmed from a finding that women from lower socioeconomic backgrounds gave birth to infants with neural tube defects at a higher rate than women who were well off and presumably had a well-rounded diet. Researches also found that babies that were conceived during the fall and winter were at an increased risk of neural tube defects, presumably because of the lack of fresh vegetables during the pregnancy. This information lead to the U.S. Public Health Service recommendation in September 1992 that all women of childbearing age consume 400 $\mu$g of folic acid daily.

In February 1996, the Food and Drug Administration recommended that certain foods that are regularly consumed by the public be fortified with folic acid. This action was taken as a preventative measure since most neural tube defects occur in the first 18–30 days of pregnancy, when most women are unaware of the pregnancy.

More recently, epidemiological studies have implicated folic acid in atherosclerosis. Researchers have found elevated levels of homocysteine, an amino acid in the blood, in people suffering from atherosclerosis. Folic acid and other B vitamins contribute to the breakdown of homocysteine and therefore may be useful for controlling atherosclerosis.

While much is known about the benefits derived from folic acid, its very low aqueous solubility have made it difficult to use and administer. Recent studies indicate that dietary supplements containing folic acid generally have failed to meet the United States Pharmacopeia (USP) Convention for dissolution, which is that 75% of the folic acid content in the supplement dissolve in an aqueous medium within one hour, the time regarded to be necessary for folic acid to pass through the stomach and into the intestine where absorption occurs. See 37 *J. Am. Pharm. Assoc.* 397 (1997) Therefore, compositions and methods for increasing the aqueous solubility of folic acid are needed so that folic acid utilization can be optimized.

BRIEF SUMMARY OF THE INVENTION

The invention provides a folic acid composition that is instantly soluble in even cold water, making possible the fabrication of pharmaceutical dosage forms that easily exceed the USP solubility standard.

One embodiment of the present invention comprises a method for making a substantially dry pharmaceutical trituration composition comprising a first compound selected from the group consisting of folic acid, folic acid analogs, and mixtures thereof; and a second compound selected from the group consisting of carbonate and bicarbonate salts, particularly Group IA metal carbonates, bicarbonates, and mixtures thereof. The second compound preferably is selected from the group consisting of sodium carbonate, sodium bicarbonate, potassium carbonate and potassium bicarbonate, and its concentration generally exceeds that of the first compound. More specifically, the relative concentrations of folic acid compound and the carbonate compound is such that the folic acid compound is not less than 1% and not more than 50% of the total of the two compounds on a dry weight basis. Other components, such as other vitamins, minerals, herbs, and other nutritional products, may be added to this trituration composition to form various other pharmaceutical and dietary supplement compositions.

The present invention also provides a method for making an aqueous-soluble folic acid-containing dosage form. The method comprises forming or obtaining the aforesaid trituration composition and adding to it one or more excipients such as binders, lubricants, diluents, humectants, disintegrants, and mixtures thereof. Tablets or other dosage forms are formed from the resulting mixture according to conventional methods. A preferred dosage form is a tablet comprising a lactose diluent, a magnesium stearate lubricant, a microcrystalline cellulose binder, a silicon dioxide desiccant, and a sodium croscarmellose disintegrant. Dosage forms may also be formulated into controlled release forms by conventional methods.

DETAILED DESCRIPTION OF PREFERRED EMBODIMENTS

As used herein, "folic acid" includes the basic folic acid moiety having the structure shown above and its analogs, preferably those analogs which are capable of being absorbed and utilized by the body. For example, and without limitation, utilization by the body may mean that the folic acid analog can be utilized as a starting point for the synthesis of methionine and certain other amino acids.

In addition to folic acid and/or folic acid analogs, the composition contains one or more carbonate or bicarbonate salts. Preferred materials are the Group 1A metal carbonates or bicarbonates, particularly sodium and potassium carbonates or bicarbonates. Examples of other carbonates that can be used include ammonium carbonate, sodium sesquicarbonate, potassium sesquicarbonate, magnesium carbonate, sodium glycine carbonate, L-lysine carbonate, and arginine carbonate.

By a "substantially dry" pharmaceutical composition is meant that, following mixing the folic acid component and the carbonate/bicarbonate component the resulting mixture contains not more than about 10 wt % water content.

The folic acid composition is made as follows. Components preferably having a purity suitable for ingestion may be screened to produce material having the desired size of granulation. Highly water-soluble compositions have been made using screens having a mesh size of not more than US #30 (600 μm). Dry compositions are then formed by mixing the components in the desired ratio, for example, where the relative concentrations of folic acid and carbonate and/or bicarbonate is such that the folic acid compound is not less than 1% and not more than 50% of the total of the folic acid and carbonate on a dry weight basis.

This basic pharmaceutical trituration composition is useful as a raw material in the fabrication of other forms of the aqueous-soluble folic acid composition. For example, it can be incorporated into a sprayable aqueous solution and so applied to processed foodstuffs such as cereals or snacks or it can be combined with other ingredients and formed into pharmaceutical dosage forms such as tablets.

As used herein, the phrase "pharmaceutical dosage form" generally means those forms described in Vol. 24 USP, p. 2107 (2000). One of ordinary skill in the art will appreciate that there are numerous dosage forms which can be used to deliver the folic acid composition to the body. The most preferred forms are tablets, capsules, multiparticulates, sachets and powders.

A tablet of the folic acid-containing composition of the present invention may be formed by conventional tableting methods, e.g., with a tablet press. This process requires that the material to be tableted be compressible and sufficiently lubricated so that it can be ejected from the tablet press without sticking and losing its shape. A detailed discussion of methods for forming tablets is found in U.S. Pat. No. 5,858,412, the disclosure of which is incorporated herein by reference.

The tableting process requires that the composition to be tableted contain a certain amount of moisture and has certain cohesive properties. These properties can be imparted to the composition by the addition of materials commonly referred to as excipients. excipients, for purposes of the present invention, are further classified as fillers (diluents), binders, glidants, desiccants, humectants, plasticizers, sorbents, suspending/viscosity-enhancing agents, sweetening agents, lubricants, wetting/solubilizing agents, and disintegrants.

Excipients may add other qualities to the tablet. For example, excipients may cause active ingredients to be released over a predetermined period of time, or they may facilitate ingestion of the tablet.

Commonly used lubricants for producing tablets that are readily ejected from the tableting press include stearates, such as magnesium and calcium stearate. Such lubricants are commonly included in the final tableted product in amounts of about 1 wt %.

The cohesive quality of a composition can be increased through the addition of one or more binding agents. As previously mentioned, binding agents impart cohesive qualities to the tablets components. Two common classes of binders are starches and sugars. Examples of sugars used as binders include maltodextrose, sucrose, glucose, dextrose, lactose, and mixtures thereof: of these, lactose is preferred.

Disintegrants also often are included in order to ensure that the tablet has an acceptable disintegration rate in an environment of use (such as the gastrointestinal tract). Typical disintegrants include starch derivatives and salts of carboxymethyl cellulose, such as sodium croscarmellose. Another example of a commonly used disintegrant is sodium starch glycolate.

Desiccants and humectants also can be added to a composition to help maintain the moisture content of the tablets. Examples of suitable desiccants include calcium chloride, calcium sulfate and silicon-based materials, such as silicon dioxide and fumed silicon. Examples of suitable humectants include glycerin, propylene glycol, hexylene glycol and sorbitol.

Additionally, some of the excipients mentioned above may serve multiple functions. For example, one of ordinary skill in the art will appreciate that lactose is both a binder and a diluent, and therefore may be added to a tablet formulation for either or both functions.

Three different preparation methods are generally used for tableting: (1) dry granulation; (2) direct compression; and (3) wet granulation. See generally, Ansel et al., *Pharmaceutical Dosage Forms and Drug Delivery Systems,* Chapter 5 ($6^{th}$ Ed. 1995), the disclosure of which is incorporated herein by reference. Each of these various methods may require that different excipients be added to the composition or that different concentrations of the same excipients be added.

Dry granulation procedures are frequently used when the active ingredient and a diluent (if necessary) is capable of forming a tablet after compression without the addition of excipients. The method includes mixing the ingredients, compacting or "slugging" large masses of the mixture into large flat tablets or pellets about one inch in diameter, breaking up the so-formed "slugs" by hand or by a mill, dry screening, lubricating and finally compressing the ingredients.

Direct compression is the most straightforward method for making tablets. This method involves forming a mixture comprising the components and then applying pressure directly to the mixture. Useful direct compression excipients generally include those having properties of fluidity and compressibility. Excipients having such properties include fillers, such as spray-dried lactose; disintegrants, such as sodium carboxymethyl starch and crosslinked carboxymethylcellulose fibers (AC-DI-SOL from FMC Corp.); lubricants, such as magnesium stearate and talc; and glidants, such as fumed silicon dioxide. Especially preferred filler excipients are dicalcium phospate, commercially available as DI-TAB from Stauffer Chemical Co., and microcrystalline cellulose, commercially available as EMCOCEL from Edward Mendell Co., Inc. and as AVICEL from FMC Corp.

Wet granulation involves mixing dry ingredients and then adding the appropriate excipients in a liquid form to form a wet granulation. The resulting wet granulation is then forced through a screen of a specified mesh size, such as a screen having a mesh size of from about 8 to about 20, to produce pellets or granules, followed by drying, dry screening, lubrication and blending, then tableting by compression.

In addition to the excipients mentioned above, additional components can be added to the folic acid compositions of the present invention to allow the active ingredient to be released over a longer period of time or to alter the rate of release or to increase the amount of the active ingredient that is absorbed by the body. See Ansel et al., Ibid. The sustained release additive may be hydrophobic or hydrophilic. Suitable materials which may be included as the sustained release additive of the present invention include sugars, starches, water-soluble cellulosics such as hydroxypropylmethylcellulose, hydrophobic cellulosics such as ethylcellulose, acrylic and methacryiic acid polymers and copolymers, zein, polylactide, a polyglycolide, a poly(lactide-co-glycolide), a polyanhydride, a polyorthoester, polycaprolactones, polyphosphazenes, polysaccharides, proteinaceous polymers, soluble derivatives of polysaccharides, soluble derivatives of proteinaceous polymers, polypeptides, polyesters and polyorthoesters. Specific examples of such include poly-1, 4-glucans, e.g., starch glycogen, amylose, amylopectin, and mixtures thereof. Additionally, the sustained release additive may be a water-soluble derivative of a poly-1, 4-glucan, including hydrolyzed amylopectin, hydroxyalkyl derivatives of hydrolyzed amylopectin, such as hydroxyethyl starch (HES), hydroxyethyl amylose, dialdehyde starch and the like.

Naturally occurring gums also can be used as sustained-release carriers. Examples of naturally occurring gums include, for example, the heteropolysaccharides and homopolysaccharides. An especially preferred heteropolysaccharide is xanthan gum, which is a high molecular weight heteropolysaccharide. Other preferred heteropolysaccharides include derivatives of xanthan gum, such as deacylated xahthan gum, its carboxymethyl ether, and its propylene glycol ester. Homopolysaccharides include galactomannan gums, which are polysaccharides composed solely of mannose and galactose. Preferred galactomahnan gums are those which are capable of crosslinking with the heteropolysaccharide. In particular, galactomannans, which have higher proportions of unsubstituted mannose regions, have been found to achieve more interaction with the heteropolysaccharide when exposed to, say, gastric fluid. Locust bean gum in an amount ranging from about 1 to 20 wt % is especially preferred as compared to other galactomannans.

Natural or synthetic gums known to those of ordinary skill in the art may also be useful as controlled-release agents for use with the compositions of the present invention. Such gums include alginic acid derivatives, carageenan, tragacanth, acacia, karaya, guar, agar, acacia, galactans, mannans and mixtures thereof. Water-swellable polymers may be used in addition to, or instead of, gums to promote controlled release of the active agent from the final formulation. Such water-swellable polymers include cellulose ethers, carboxyvinyl polymers and the like. The combination of xanthan gum with locust bean gum is an especially preferred gum combination. In certain embodiments the controlled-release properties are optimized when the ratio of heteropolysaccharide gum to galactomannan gum is from about 3:1 to about 1:3, and most preferably about 1:1. However, in this embodiment, the additive may comprise from about 1 wt % to about 99 wt % heteropolysaccharide gum and from about 99 wt % to about 1 wt % homopolysaccharide gum.

The controlled-release formulation may include a pharmaceutically acceptable substance which may alter, e.g., prolong or increase, the release rate of the active agent from the formulation upon exposure to an aqueous environment of use, such as gastric fluid or a dissolution medium. The controlled-release additive in oral dosage forms of the present invention may be present from about 1 to about 99 wt %; preferably from about 1 to about 80 wt %. Suitable substances that may be incorporated into the trituration composition of the present invention include, for example, monovalent or multivalent metal cations including, for example, alkali metal and/or alkaline earth metal sulfates, chlorides, borates, bromides, citrates, acetates and lactates. Specific examples of suitable salts include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate, sodium fluoride, and combinations thereof. In a preferred embodiment, such release-modifying agents are bivalent.

Mixtures of any of the foregoing, and other pharmaceutically acceptable materials currently known to persons of ordinary skill in the art also may be used in accordance with the present invention.

Coating formulations also can be used to prolong release of the active ingredient as well as to facilitate tablet ingestion. See generally, Ansel et al., Ibid. In certain preferred embodiments of the present invention, the coating includes a hydrophobic polymer; e.g., a pharmaceutically acceptable acrylic polymer, including but not limited to acrylic- and methacrylic acid copolymers; methyl methacrylate copolymers; ethoxyethyl methacrylates; cynaoethyl methacrylate; aminoalkyl methacrylate copolymer; poly(acrylic acid); poly(methacrylic acid); methacrylic acid alkylamide copolymer; polymethacrylate; poly(methyl methacrylate); polyacrylamide; aminoalkyl methacrylate copolymer; poly (methacrylic acid anhydride); glycidyl methacrylate copolymers; ethyl cellulose; waxes; fatty acids; shellac; wax-type substances, including hydrogenated castor oil and hydrogenated vegetable oil; synthetic waxes; hydrogenated fats; stearic acid; stearyl alcohol; and mixtures thereof. Examples of suitable commercially available polymethacrylates include EUDRAGIT RS and/or RL, commercially available from Rohm Tech, Inc.

The following examples are provided to illustrate certain features of working embodiments of the present invention. The scope of the invention is not to be limited to those particular features exemplified.

EXAMPLE 1

This example describes a method for preparing the water-soluble folic acid trituration composition of the present invention. Eleven kg of USP-grade folic acid and 89 kg of sodium bicarbonate, each with a water content of about 8 wt % were mixed to provide a weight ratio of folic acid to sodium bicarbonate of about 1:8. Mixing was conducted in a planetary mixer (Model 6-R-B, Grove Dale Corp., San Jose, Calif.) for 15 minutes at 14 rpm. The composition was then milled through a 33-mesh sieve at 3500 rpm, using a Fitz Mill Model DS-6 (Fitz Patrick Co., Elmhurst, Ill.).

EXAMPLE 2

The water solubility of the trituration composition of Example 1 was tested in accordance with the procedures set forth in Vol. 24 USP p. 2254 (2000). One gram of the folic acid composition of Example 1 was weighed and transferred to a 100-ml volumetric flask. Fifteen ml of deionized water was added at 20° C. with gentle swirling, causing the folic acid composition to completely dissolve within seconds, indicated by a clear slightly yellowish solution.

According to the definitions of solubility as recited in the USP reproduced as Table 1 below, the trituration composition of the present invention can be rated as "soluble" in water.

TABLE 1

| Descriptive Term | Parts of Solvent Required For 1 Part of Solute |
|---|---|
| Very Soluble | Less than 1 |
| Freely Soluble | From 1 to 10 |
| Soluble | From 10 to 30 |
| Sparingly Soluble | From 30 to 100 |
| Slightly Soluble | From 100 to 1000 |
| Very Slightly Soluble | From 1000 to 10,000 |
| Practically Insoluble | 10,000 and over |

EXAMPLE 3

This example used the same solubility testing procedure as in Example 2 except that the solvent was 0.05 M citrate buffer at a pH of 6.0. Citrate buffer is another solvating medium which has been adopted as a dissolution standard by the USP. 24 USP Supplement 1, p. 2730 (2000). The citrate buffer solution was added to a volumetric flask containing 1 gram of the composition of Example 1 while stirring. Fifteen ml of buffer were needed to completely dissolve the folic acid composition. Thus, the folic acid composition of the present invention can also be rated as "soluble" in the USP-proposed standard medium.

EXAMPLE 4

This example describes the formation of tablets from the water-soluble folic-acid trituration composition of Example 1. Preparing the folic acid/bicarbonate composition prior to mixing with the excipients will cause better distribution of the folic acid in the blend, resulting in greater content uniformity. Tablets containing 8.0 mg of the trituration composition containing 800 $\mu$g (0.8 mg) of folic acid and the tableting excipients stated in Table 2 were made using a direct compression technique.

TABLE 2

| CONCENTRATION (mg/tablet) | COMPONENT |
|---|---|
| 8.0 mg | Folic acid Trituration |
| 177.0 mg | Lactose |
| 50.0 mg | Microcrystalline cellulose |
| 5.0 mg | Croscarmellose sodium |
| 3.0 mg | Magnesium stearate |
| 2.0 mg | Silicon dioxide |

EXAMPLE 5

Utilizing the High-Pressure Liquid Chromatography (HPLC) assay set forth in Vol. 24 USP p. 753 (2000), the USP folic acid label claim of the tablets of Example 4 was tested. A mobile phase was created by adding 35.1 g of sodium perchlorate, 1.4 g of monobasic potassium phosphate, 7 ml of 1 N potassium hydroxide and 40 ml of methanol to a 1 L volumetric flask. The mixture was then brought to a final volume of 1 L and mixed thoroughly. The pH was adjusted to 7.2 using either 1 M potassium hydroxide or phosphoric acid as necessary.

A 3.9 mm×30 cm L-1 (C-18) Waters No. WAT027324 separation column was used, maintained at 25° C. and at a flow rate of 2 ml/min. To ensure that the HPLC system was working within the USP-specified parameters, tests were done by injecting 10 $\mu$l of the system suitability solution. Injection volume for dissolution standard solution and for dissolution test solution were both 100 $\mu$l. The value of resolution must be not less than 3.6 between folic acid and related compound A. The Relative Standard Deviation (RSD) between replicates must not be more than 2.0%. The wavelength of the UV detector was set at 254 nm.

A solvent was made for the dilution of the system suitability solution. This solvent contained 5 g of sodium perchlorate and 10 ml of ammonium hydroxide diluted to 500 ml in a volumetric flask. All solutions were protected from light. The system suitability solution comprised 10 mg of USP-grade folic acid as a reference standard (RS) and 10 mg of USP-grade folic acid-related compound A diluted in solvent in a 10 ml amber volumetric flask.

The standard was prepared by weighing 20 mg of the folic acid RS (corrected for water content) into a 100 ml volumetric flask. Approximately 20 ml of water and 180 mg of sodium bicarbonate were then added. These materials were dissolved and diluted to volume with water. Two ml of this solution was transferred to a 250 ml volumetric flask and diluted to volume with water.

The test samples comprised six randomly selected tablets from the batch prepared in Example 4. Each tablet was placed into individual. vessels of the dissolution apparatus and dissolution tests were performed in accordance with USP-specified protocol. After 45 minutes samples were taken from each vessel and loaded into the HPLC injector module.

The data was then collected and the percent of the label claim of folic acid dissolved was determined using the following formula. The results are shown in Table 3.

$$\frac{Sample\ Response}{Standard\ Response} \times \frac{4 \times STD \times F}{LC} = \%\ of\ Label\ Claim$$

where
Sample Response=Area of the HPLC peak of the sample
Standard Response=Area of the HPLC peak of the RS
STD=Actual weight in mg of RS (20.1 mg)
F=Purity factor (including moisture content) of the RS (0.90005)
LC=Labeled amount of folic acid per tablet (0.8 mg)

TABLE 3

| TABLET NO. | SAMPLE RESPONSE | STANDARD RESPONSE* | LABEL CLAIM** |
|---|---|---|---|
| 1 | 149357 | 134405 | 101% |
| 2 | 149842 | 134405 | 101% |
| 3 | 164297 | 134405 | 111% |
| 4 | 162367 | 134405 | 109% |
| 5 | 164070 | 134405 | 110% |
| 6 | 159780 | 134405 | 108% |

*Average of four with relative standard deviation of 0.7%
**Average = 107%

According to the USP, the percent of label claim amount of folic acid must be at least 80%. Vol 24 USP p. 753 (2000). Thus, the values shown in Table 3 indicate that the tablets made with the water-soluble folic acid trituration composition of the present invention exceeded by far USP-mandated dissolution requirements.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A water-soluble folic acid composition consisting essentially of a substantially dry mixture of
   (a) a first compound selected from the group consisting of folic acid, folic acid analogs, and mixtures thereof; and
   (b) a second compound selected from the group consisting of carbonate and bicarbonate salts, and mixtures thereof.

2. The composition of claim 1 wherein said carbonate and bicarbonate salts are selected from the group consisting of ammonium carbonate, sodium bicarbonate, sodium sesquicarbonate, potassium carbonate, potassium bicarbonate, potassium sesquicarbonate, sodium glycine carbonate, L-lysine carbonate, magnesium carbonate and arginine carbonate.

3. A water-soluble folic acid composition, consisting essentially of a substantially dry mixture of
   (a) a first compound selected from the group consisting of folic acid, folic acid analogs, and mixtures thereof; and
   (b) a second compound selected from the group consisting of Group IA metal carbonates, bicarbonates and mixtures thereof.

4. The composition of claim 1 or 3 wherein the concentration of said second compound exceeds the concentration of said first compound.

5. The composition of claim 1 or 3 wherein the relative concentrations of said first compound and said second compound are such that said first compound is not less than 1 wt % and not more than 50 wt % of the total weight of said first and second compounds.

6. A water-soluble folic acid-containing dosage form consisting essentially of:
   (a) a substantially dry mixture comprising (i) a first compound selected from the group consisting of folic acid, folic acid analogs, and mixtures thereof, and (ii) a second compound selected from the group consisting of Group IA metal carbonates, bicarbonates and mixtures thereof,
   (b) at least one pharmaceutically acceptable excipient; and
   (c) at least one ingredient selected from the group consisting of a vitamin, a mineral and an herb.

7. The dosage form of claim 6 wherein said at least one excipient is selected from the group consisting of diluents, binders, desiccants, humectants, plasticizers, sorbents, suspending/viscosity-enhancing agents, sweetening agents, lubricants, wetting/solubilizing agents, and disintegrants.

8. The dosage form of claim 7 wherein said diluent is selected from the group consisting of lactose, sucrose and dextrose.

9. The dosage form of claim 7 wherein said lubricant is magnesium stearate.

10. The dosage form of claim 7 wherein said binder is microcrystalline cellulose.

11. The dosage form of claim 7 wherein said desiccant is selected from the group consisting of silicon dioxide, fumed silicon and mixtures thereof.

12. The dosage form of claim 7 wherein said disintegrant is selected from the group consisting of croscarmellose sodium and sodium starch glycolate.

* * * * *

UNITED STATES PATENT AND TRADEMARK OFFICE
CERTIFICATE OF CORRECTION

PATENT NO. : 6,248,361 B1
DATED : June 19, 2001
INVENTOR(S) : Johnson et al.

It is certified that error appears in the above-identified patent and that said Letters Patent is hereby corrected as shown below:

Column 3,
Line 44, change "excipients" to -- Excipients --

Column 5,
Line 3, change "methacryiic" to -- methacrylic --
Line 24, change "xahthan" to -- xanthan --
Line 25, remove hyphen between "and" and "its"
Lines 27 and 28, change "glactomahnan" to -- glactomannan --

Column 8,
Line 22, delete period following "individual"

Signed and Sealed this

Sixteenth Day of April, 2002

Attest:

Attesting Officer

JAMES E. ROGAN
Director of the United States Patent and Trademark Office